(12) United States Patent
Pettaway (10) Patent No.: US 7,544,331 B1
(45) Date of Patent: Jun. 9, 2009

(54) VEHICLE LIGHTER AIR FRESHENER

(76) Inventor: Romano Pettaway, 720 Doby La., Saraland, AL (US) 36571

( * ) Notice: Subject to any disclaimer, the term of this patent is extended or adjusted under 35 U.S.C. 154(b) by 278 days.

(21) Appl. No.: 11/483,512

(22) Filed: Jul. 10, 2006

(51) Int. Cl.
*A61L 9/00* (2006.01)

(52) U.S. Cl. .................. 422/125; 422/123; 392/386; 392/391; 392/394

(58) Field of Classification Search ............ 422/123, 422/125; 392/386, 391, 394
See application file for complete search history.

(56) References Cited

U.S. PATENT DOCUMENTS

| | | | |
|---|---|---|---|
| 3,006,042 A | 10/1961 | Calandra | |
| 4,574,181 A | 3/1986 | Spector | |
| 4,604,245 A | 8/1986 | Gutierrez | |
| 5,038,394 A | 8/1991 | Hasegawa et al. | |
| 5,222,186 A | 6/1993 | Schimanski et al. | |
| 5,314,669 A * | 5/1994 | Hamilton | 422/305 |
| 5,373,581 A * | 12/1994 | Smith | 392/390 |
| 5,394,506 A * | 2/1995 | Stein et al. | 392/395 |
| 5,484,086 A | 1/1996 | Pu | |
| 5,710,406 A | 1/1998 | Garris et al. | |
| 6,085,027 A | 7/2000 | Sexton | |
| 6,197,263 B1 * | 3/2001 | Blount | 422/125 |
| 6,249,645 B1 * | 6/2001 | Smith | 392/403 |
| 6,379,178 B1 * | 4/2002 | Jones et al. | 439/501 |
| 6,413,476 B1 * | 7/2002 | Barnhart | 422/124 |
| 2007/0107278 A1 * | 5/2007 | Norwood | 40/424 |

FOREIGN PATENT DOCUMENTS

| | | |
|---|---|---|
| DE | 10305480 | 8/2004 |
| EP | 1.097.723 | 5/2001 |
| GB | 2.377.174 | 1/2003 |
| WO | WO03/077961 | 9/2003 |

* cited by examiner

*Primary Examiner*—Sean E Conley
(74) *Attorney, Agent, or Firm*—Michael I Kroll (57) ABSTRACT

An electric automobile air freshening device that has an oil chamber for receiving various scented oils that are vaporized when a heating element is thermally energized when the related 12 VAC plug is inserted in a cigarette lighter receptacle. The plug may be integral with the housing or detachable via a retractable cord.

6 Claims, 11 Drawing Sheets

VEHICLE LIGHTER AIR FRESHENER

BACKGROUND OF THE INVENTION

Field of the Invention

The present invention relates generally to air freshener devices and, more specifically, to an oil-based air freshener for motor vehicles that comprises a fragrance housing with a 12V plug projecting therefrom that plugs into the lighter of the vehicle to supply power to an electric heater element enclosed therein to heat the oil. The oil is retained in a chamber with the heater element and the chamber is accessed by removing the cover of the fragrance housing. The fragrance is released when heated by the heating element and passes through a plurality of fragrance egress apertures disposed in the cover.

An on/off switch may also be included as well as a heat control means that will reduce a greater amount of fragrance into the ambient air when the heat is turned up.

Also shown are alternates of the present invention wherein the 12V plug is not fixed but is removably attached to the housing and remain in electrical communication with each other when separated by a retractable cord similar to those found in vacuum cleaners. The removable plug allows the user to selectively and removably place the fragrance housing in an appropriate location on the dashboard or elsewhere when the ashtray and lighter are located in a console or when the configuration of the ashtray would cause the presence of the present invention to be an obstruction.

SUMMARY OF THE PRESENT INVENTION

A primary object of the present invention is to provide an electric automobile air freshening device that is plugged into a cigarette lighter or other 12 VAC receptacle to supply power to a heating element within a housing for the purpose of vaporizing an aromatic oil contained therein which is emitted into the ambient interior of the vehicle to provide a pleasant fragrance of the users choice therein.

Another object of the present invention is to provide an electric automobile air freshening device having a 12 VAC plug projecting from the housing that has electrical contacts that are in electrical communication with a heating coil that is energized once the plug is inserted into the cigarette lighter receptacle.

Yet another object of the present invention is to provide an electric automobile air freshening device wherein the heating coil is in thermal communication with the heater element and transfers heat thereto for vaporizing the scented oil in the oil chamber.

Still yet another object of the present invention is to provide an electric automobile air freshening device having a 12 VAC plug that is detachable from the housing and remains in electrical communication therewith via a retractable cord.

Another object of the present invention is to provide an electric automobile air freshening device including a filter element disposed between the cover of the housing and the scented oil in the oil chamber.

Yet another object of the present invention is to provide an electric automobile air freshening device that is simple and easy to use.

Still another object of the present invention is to provide an electric automobile air freshening device that is inexpensive to manufacture and operate.

Additional objects of the present invention will appear as the description proceeds.

The present invention overcomes the shortcomings of the prior art by providing an electric automobile air freshening device that has an oil chamber for receiving various scented oils that are vaporized when a heating element is thermally energized when the related 12 VAC plug is inserted in a cigarette lighter receptacle. The plug may be integral with the housing or detachable via a retractable cord.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

LIST OF REFERENCE NUMERALS

DESCRIPTION OF THE REFERENCED NUMERALS

Turning now descriptively to the drawings, in which similar reference characters denote similar elements throughout the several views, the figures illustrate the Electric Automotive Air Freshener Device of the present invention. With regard to the reference numerals used, the following numbering is used throughout the various drawing figures.

- 10 Electric Automotive Air Freshener Device of the present invention
- 12 fragrance housing
- 14 12 VAC plug
- 16 electrical contact
- 18 cover of 12
- 20 fragrance egress apertures
- 22 oil chamber of 12
- 24 oil heating element
- 26 heating coil
- 28 scented oil
- 30 12 VAC receptacle
- 32 motor vehicle
- 34 dashboard
- 36 user
- 38 on/off temperature control switch
- 40 retractable cord 42 threaded attachment means
44 spring loaded locking spool
46 axle of 44
48 electrical connection
50 engaging means
52 filter element

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

Figure 1:
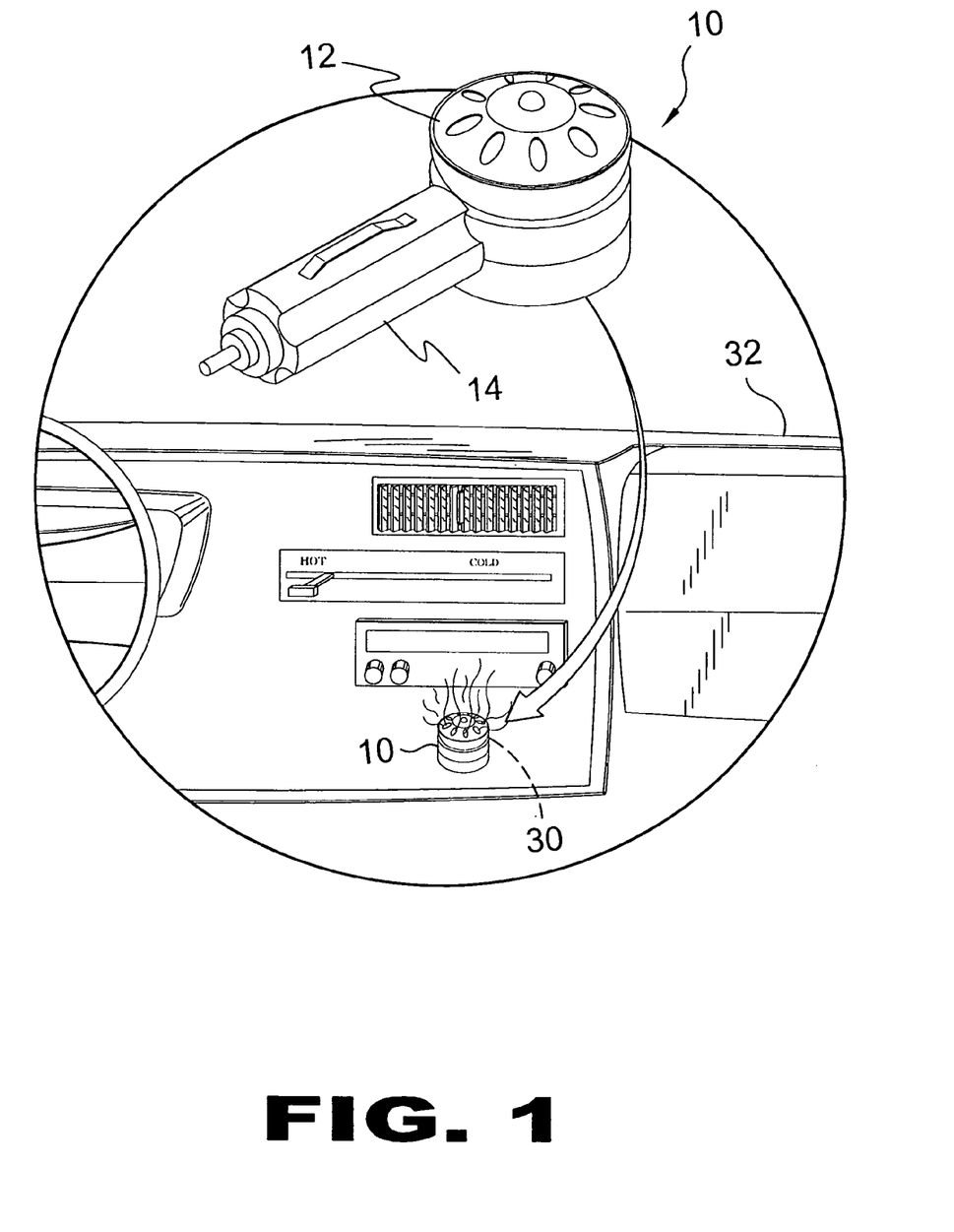
FIG. 1 is an illustrative view of the present invention in use.

FIG. 1 is an illustrative view of the present invention in use. The present invention is an electrically heated oil-based air freshener 10 for use with the cigarette lighter 30 of a motor vehicle 32. The heated auto air freshener 10 comprises a fragrance housing 12 with a 12 VAC plug 14 projecting from the side thereof.

Figure 2:
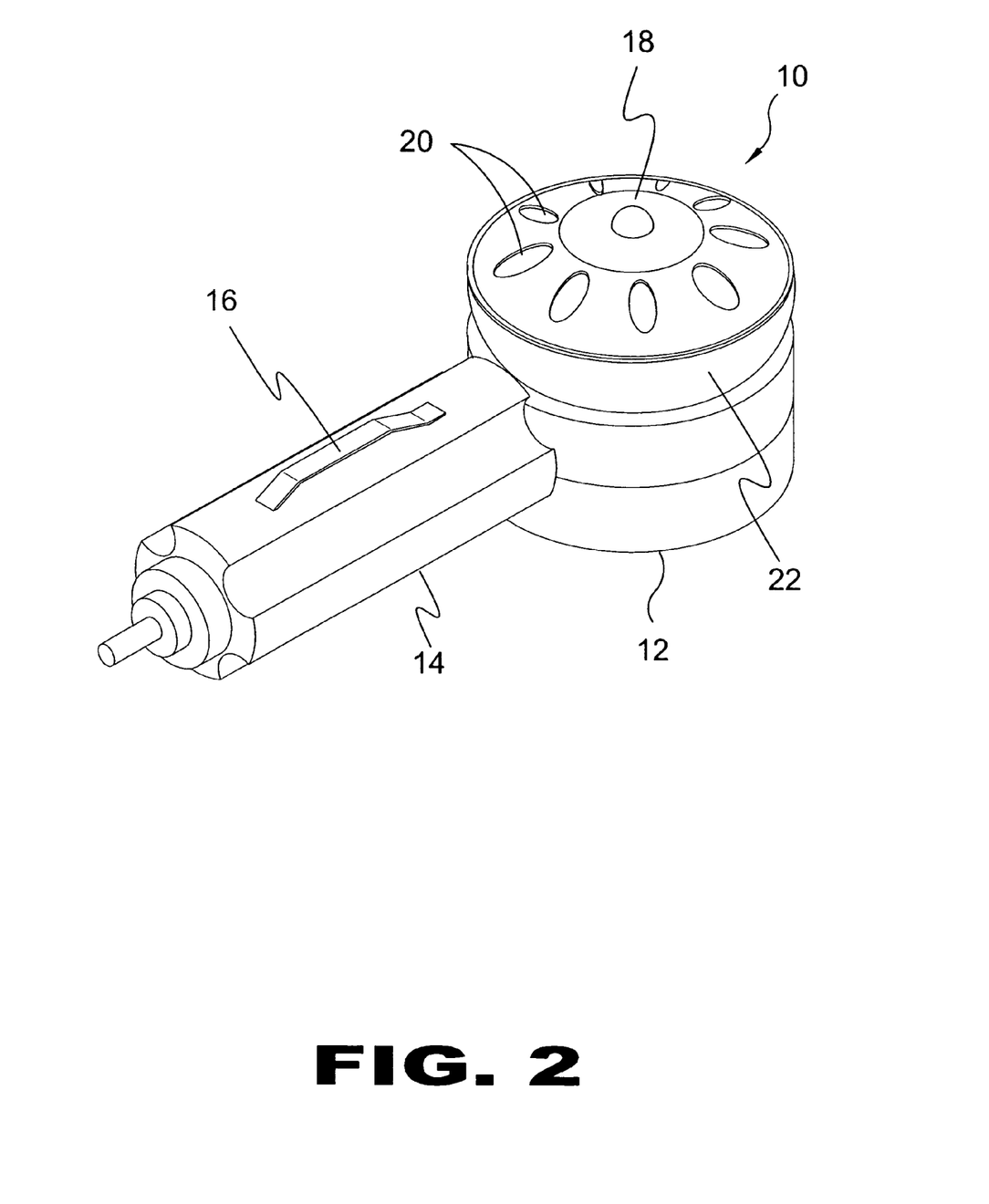
FIG. 2 is a perspective view of the present invention.

FIG. 2 is a perspective view of the present invention 10. Shown are the electrical contacts 16 of the 12 VAC plug 14 and the removable cover 18 installed on the housing 12. The scented oil within the oil chamber 22 of the housing 12 is vaporized when heated and is released in the ambient environment through the fragrance egress apertures 20 in the cover 18.

Figure 3:
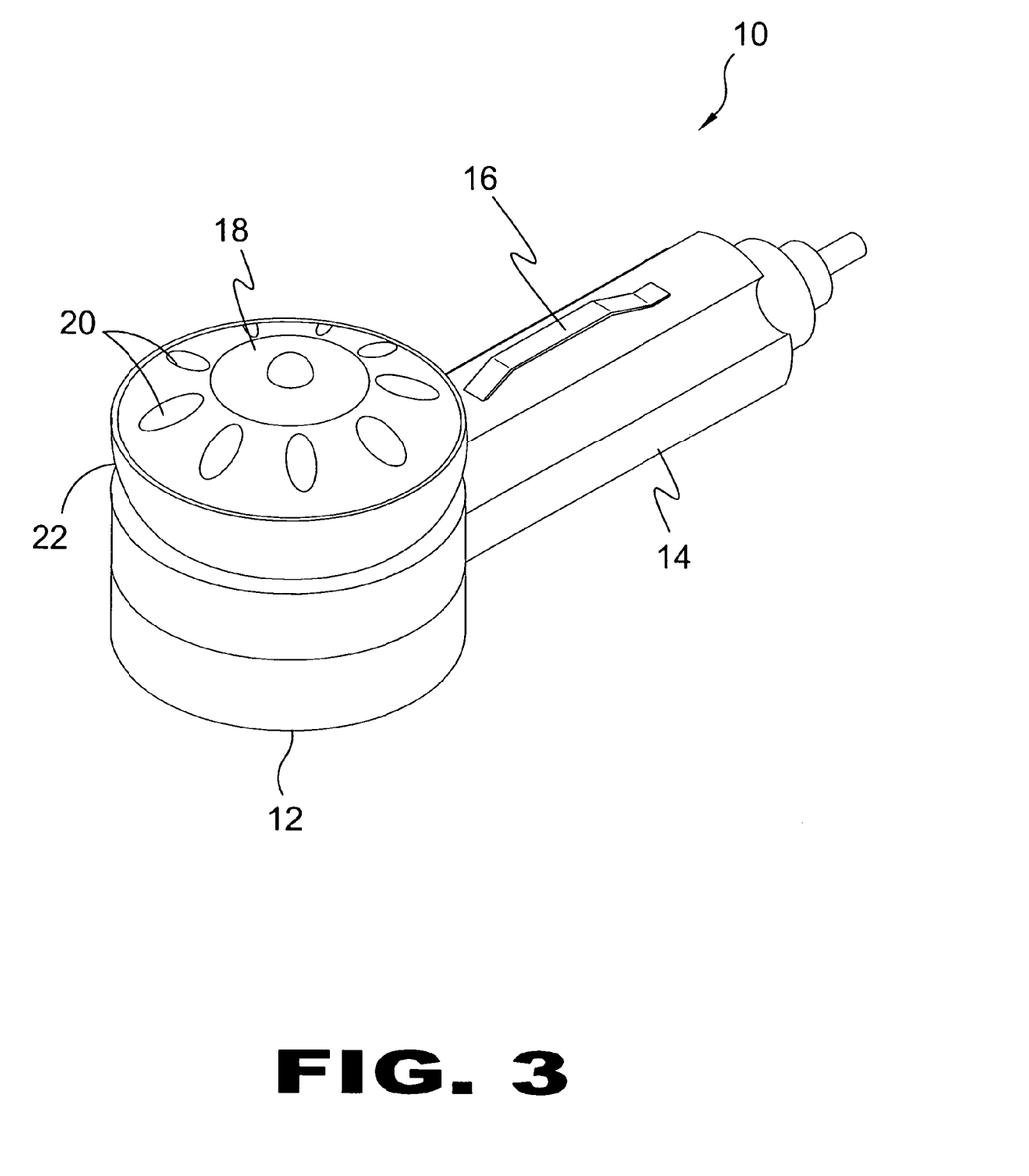
FIG. 3 is a perspective view of the present invention.

FIG. 3 is a perspective view of the present invention 10. Shown are the electrical contacts 16 of the 12 VAC plug 14 and the removable cover 18 installed on the housing 12. The scented oil within the oil chamber 22 of the housing 12 turns to a fragrant gaseous state when heated and is released in the ambient environment through the fragrance egress apertures 20 in the cover 18.

Figure 4:
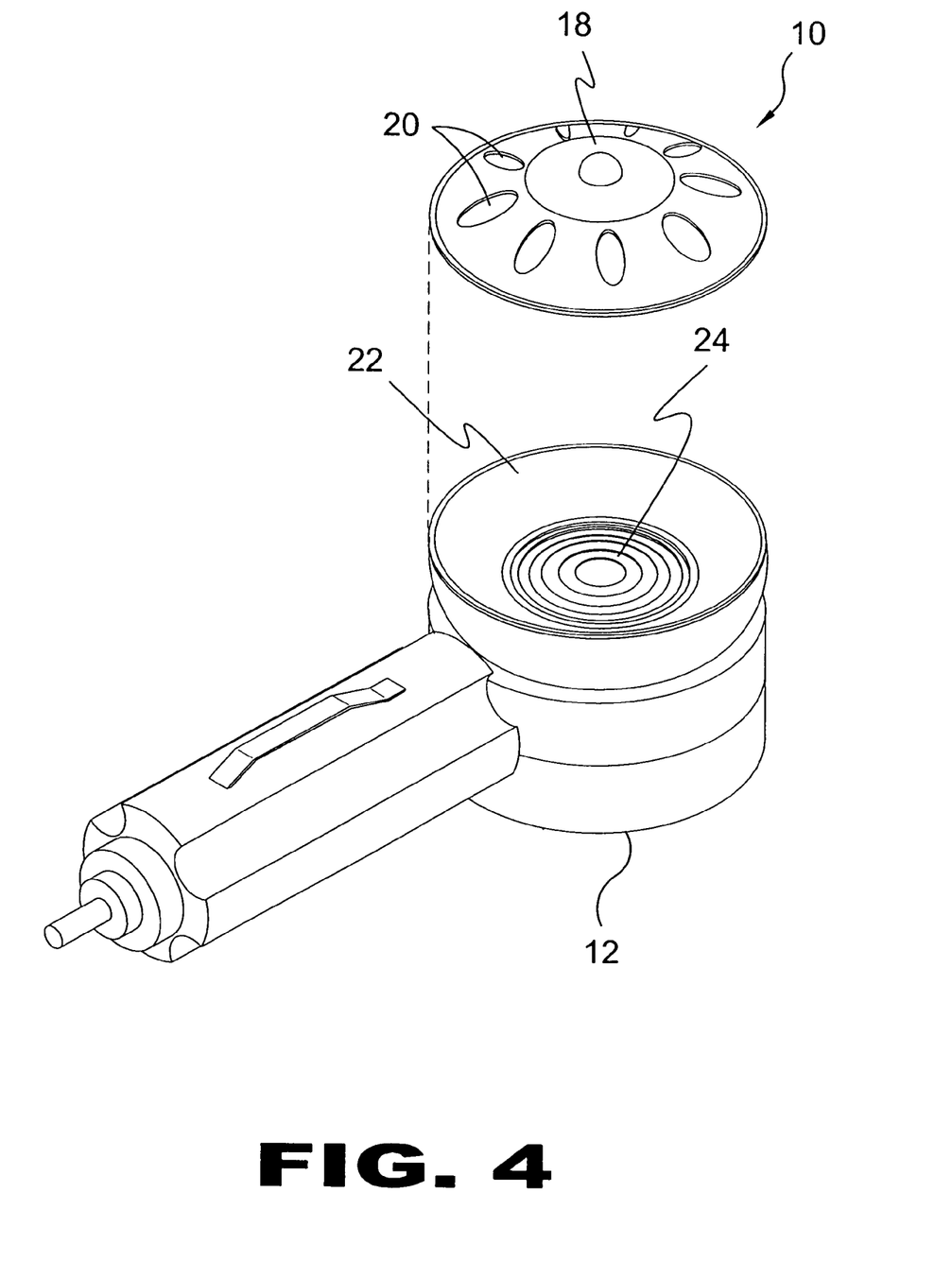
FIG. 4 is a perspective view of the present invention with the cover removed.

FIG. 4 is a perspective view of the present invention 10 with the cover 18 removed. The scented oil within the oil chamber 22 of the housing 12 is vaporized when heated 24 and is released in the ambient environment through the fragrance egress apertures 20 in the cover 18.

Figure 5:
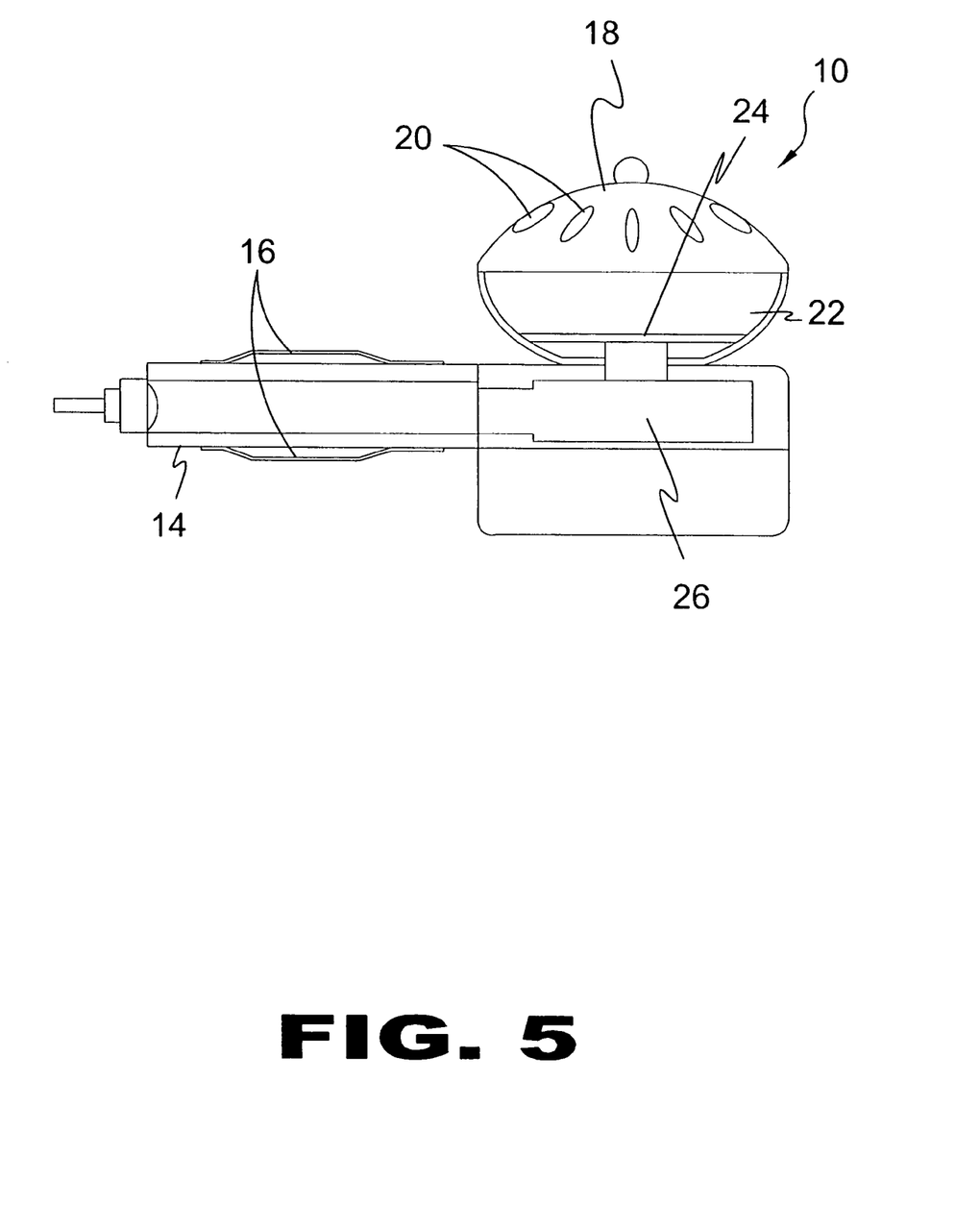
FIG. 5 is a sectional view of the present invention.

FIG. 5 is a sectional view of the present invention 10. When the 12 VAC plug 14 is inserted into the receptacle, electricity is received from the electrical contacts 16 and delivered to the heating coil 26 which is thermal communication with the oil heating element 24 in the oil chamber 22. The oil heating element 24 gasifies the scented oil in the oil chamber 22 and the fragrant vapors passes the fragrance egress apertures 20 of the cover 18 into the ambient environment.

Figure 6:
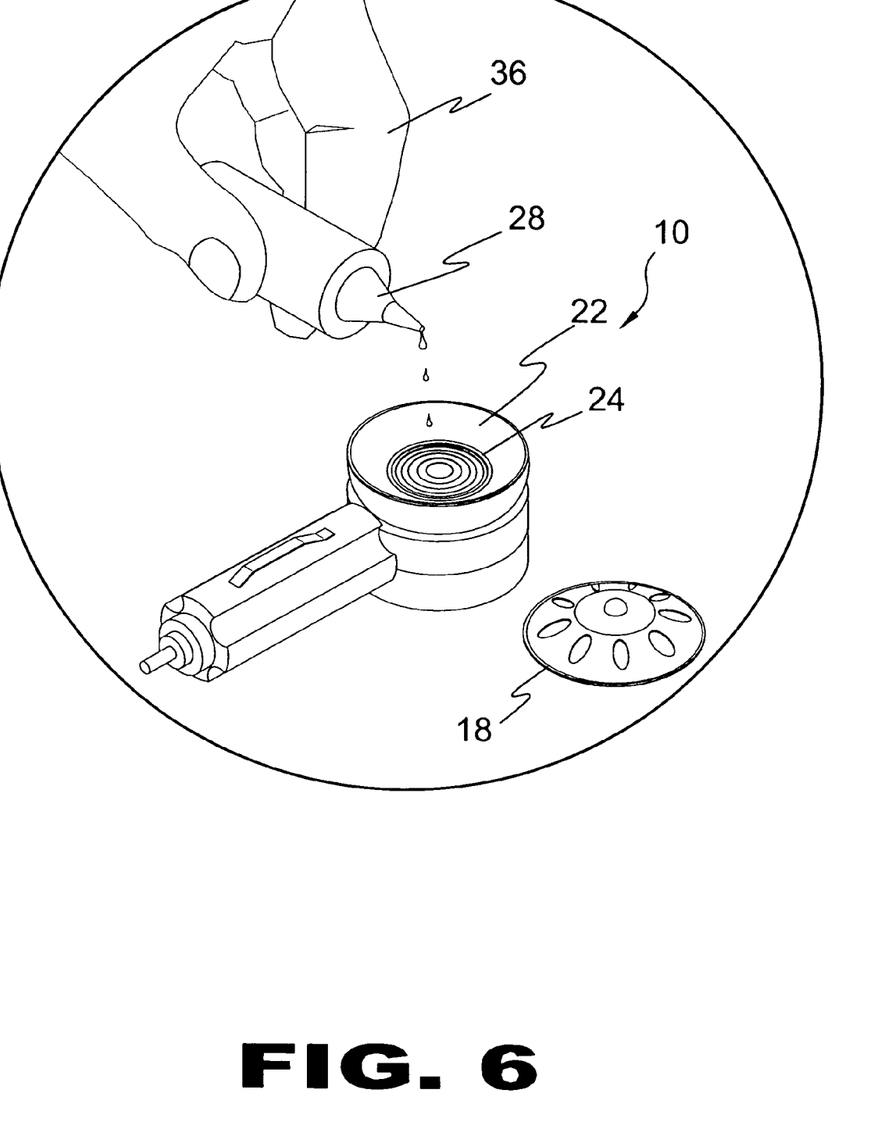
FIG. 6 is an illustrative view of the present invention.

FIG. 6 is an illustrative view of the present invention. Shown is the present invention 10 with the cover 18 removed and the user 36 delivering scented oil 28 to the oil chamber 22 and its associated oil heating element 24. The scented oils 28 are available in a wide variety of fragrances to provide the user 36 ample choices.

Figure 7:
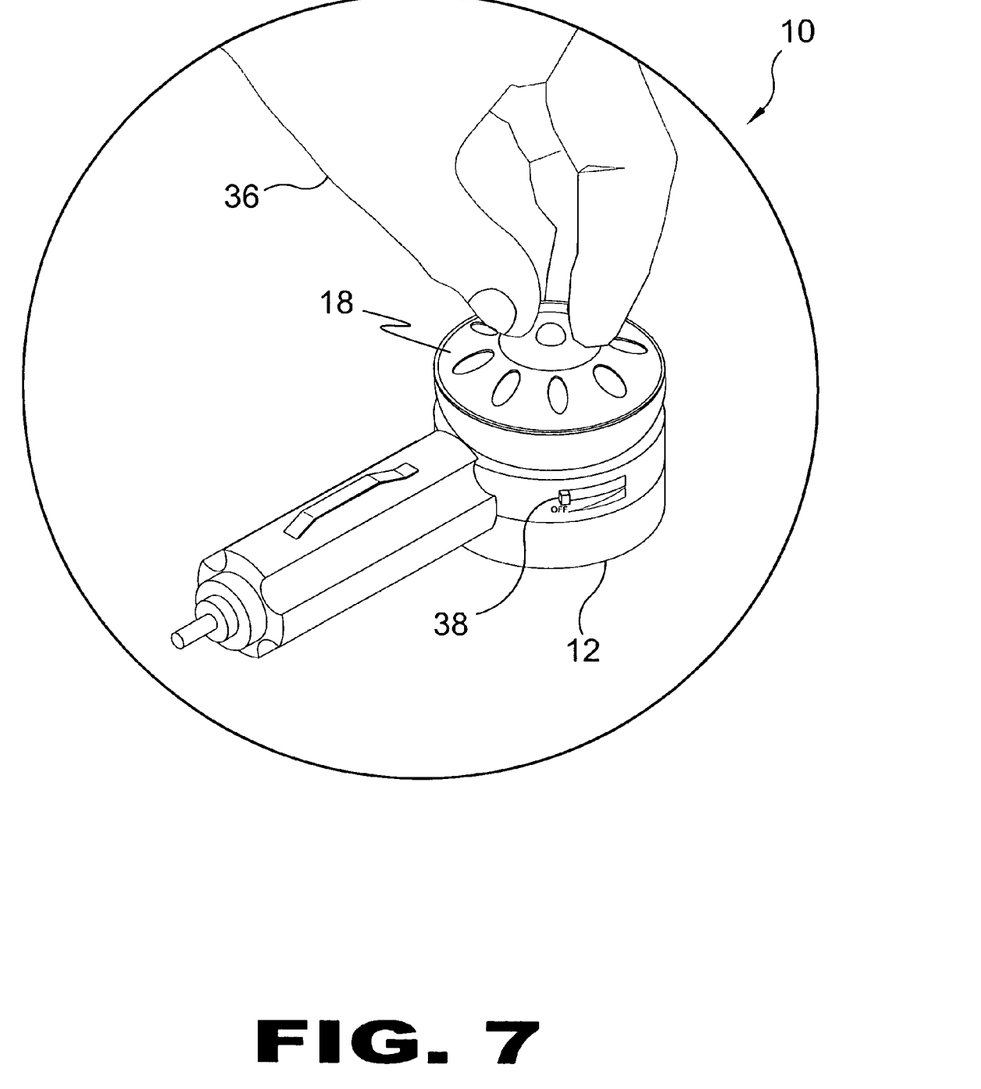
FIG. 7 is an illustrative view of the present invention.

FIG. 7 is an illustrative view of the present invention 10, shown is the user 36 returning the cover 18 to the top of the housing 12. Shown is the housing 12 having an optional on/off temperature control slide switch 38. The present invention 10 may include just an on/off switch or a temperature control means or any combination thereof. Any suitable configuration of buttons, toggle switches and the like may be employed. Increasing the heat applied to the oil increases the rate of evaporation and the strength of the fragrant vapors emitted into the vehicle, thus the inclusion of a temperature control means serves to allow the user 36 to adjust the intensity of the emitted fragrance accordingly.

Figure 8:
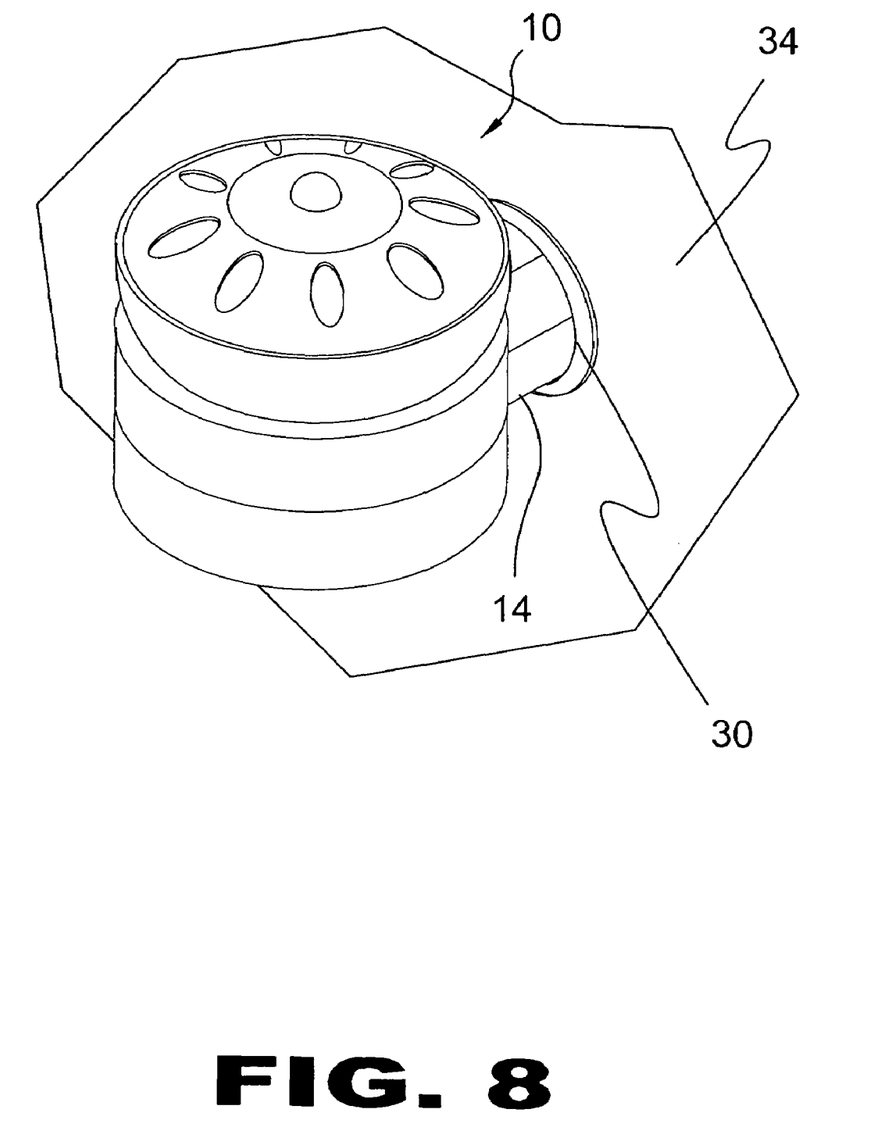
FIG. 8 is a detailed view of the present invention.

FIG. 8 is a detailed view of the present invention 10 in use. Shown is the 12 VAC plug 14 inserted into the 12 VAC cigarette lighter 30 in the dashboard 34.

Figure 9:
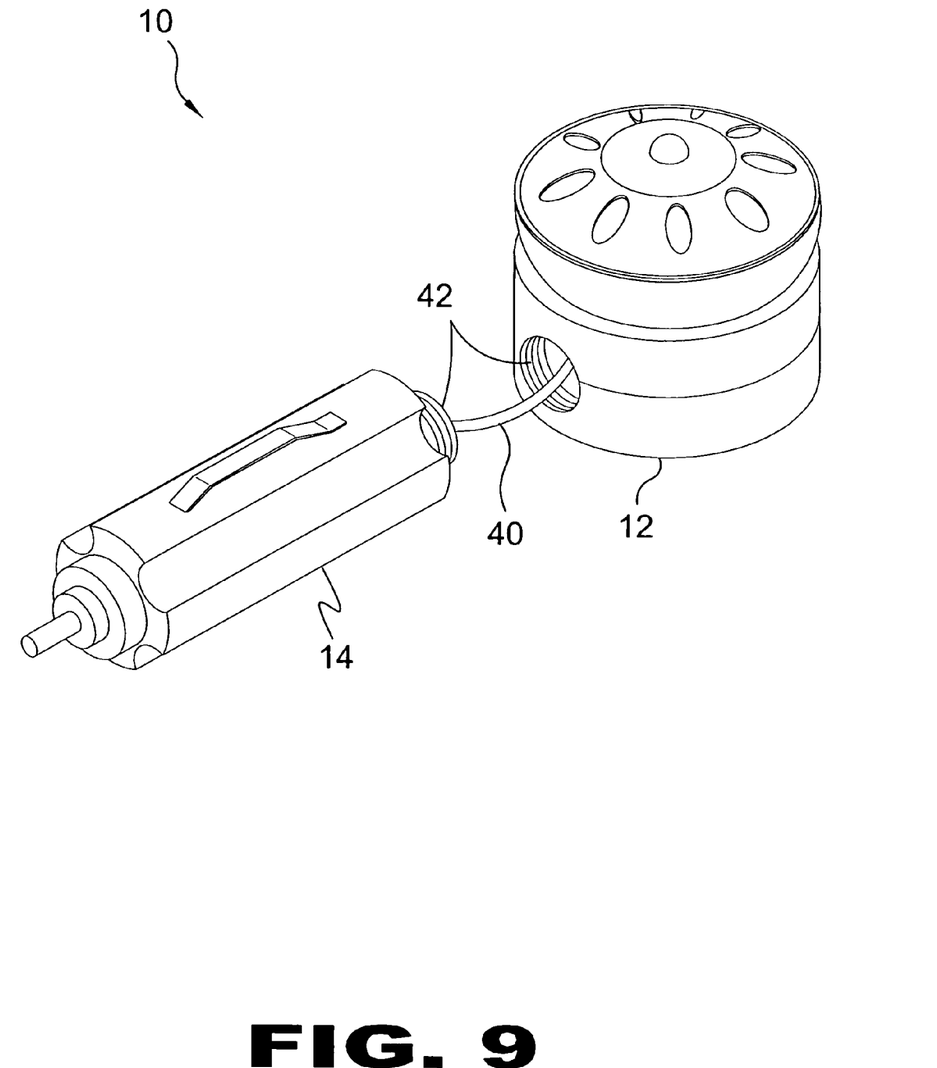
FIG. 9 is a perspective view of an alternate of the present invention.

FIG. 9 is a perspective view of an additional element of the present invention. Shown is the present invention 10 wherein the 12 VAC plug 14 is detachable from the housing 12 and the electrical communication is maintained via a retractable cord 40. A threaded attachment means 42 is depicted although any appropriate attachment means may be employed.

Figure 10:
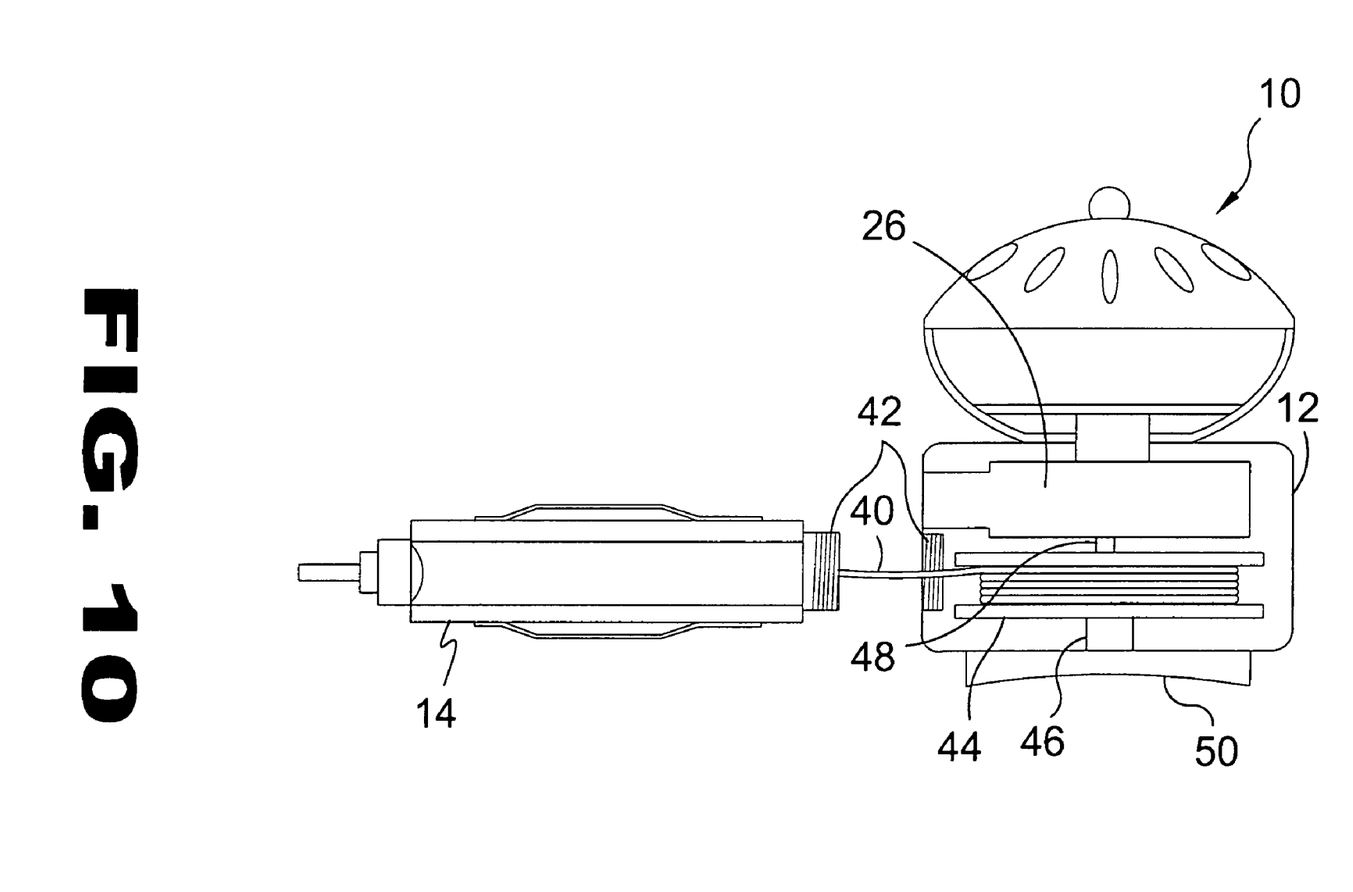
FIG. 10 is a sectional view of an alternate of the present invention.

FIG. 10 is a sectional view of the additional element of the present invention introduced in FIG. 9. Shown is the present invention 10 wherein the 12 VAC plug 14 is detached from the housing 12 and the electrical communication is maintained via a retractable cord 40. A threaded attachment means 42 is depicted although any appropriate attachment means may be employed. The cord 40 is coiled around a spring-loaded locking spool 44 similar to those used with vacuum cleaners. The spool 44 rotates on an axle 46 and has an electrical connection 48 with the heating coil 26. The bottom of the housing 12 includes an engaging means 50 such as a suction cup or hook and loop fastener elements for securing the housing 12 to a surface such as a dashboard or console. The detachable plug 14 and retractable cord 40 are advantageous when the lighter is disposed within the ashtray and the presence of the housing 12 would prove to be an obstruction to the usage thereof.

Figure 11:
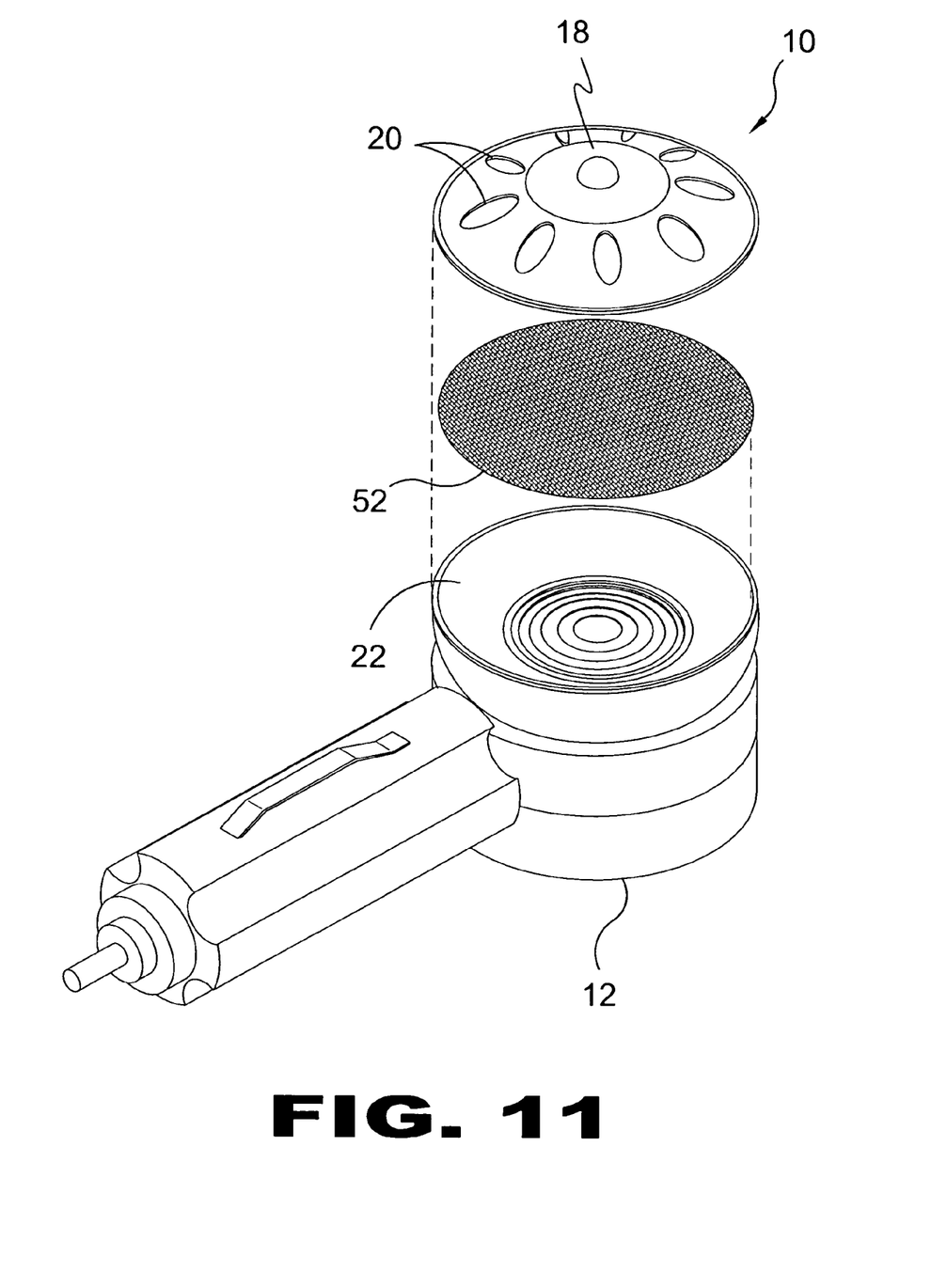
FIG. 11 is a perspective view of an additional element of the present invention.

FIG. 11 is an exploded perspective view of an additional element of the present invention 10. Included is a replaceable filter element 52 that is porous enough to allow the passage of the fragrant vapors but is too dense to permit the passage of the scented oil therethrough. The filter element 52 is disposed between the fragrance egress apertures 20 in the cover 18 and the scented oil in the oil chamber 22 of the housing 12.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention

What is claimed is new and desired to be protected by Letters Patent is set forth in the appended claims:

1. An electrical automotive air freshener comprising:
   a) a housing comprising;
      i) a bowl shaped oil chamber for storing and vaporizing scented oil, said bowl shaped oil chamber mounted on a top surface of a lower housing;
      ii) a removable cover for providing access to and securing said chamber;
      iii) fragrance egress openings in said cover to allow vaporized oil to exit said oil chamber
      iv) a heating element in said lower housing penetrating a bottom of said oil chamber in thermal communication with said oil chamber;

v) a heating coil in said lower housing in thermal communication with said heating element;

b) a plug projecting from said lower housing adapted to plug into a 12 volt receptacle in an automotive vehicle; and c) contacts on said plug in electrical communication with said heating coil;

d) said plug detachable from said housing and remains in electrical communication with said heater via a retractable cord assembly; and e) said retractable cord assembly comprises:

i) a spring loaded locking spool disposed in said housing;

ii) an axle extending vertically below said spool and to which said spool is rotatively attached;

iii) an electrical connection extending above said spool and communicating between said spool and said heating coil, said electrical connection being in axial alignment with said axle;

iv) a retractable cord having a first end terminating within said plug and in electrical communication with said contacts thereon and a second end terminating at said spool and in electrical communication with said electrical connection; and v) engagement means on a bottom wall of said lower housing for securing said lower housing to a surface.

2. The electrical automotive air freshener recited in claim 1, wherein said lower housing and said plug further include mating attachment means for quickly and easily engaging and disengaging said plug from said housing, whereby when said plug is disengaged from said lower housing and said cord is extended to a desired length a lock mechanism locks said spool, and whereby said cord is retraced by pulling thereby releasing the lock mechanism on said spool so that a spring in said spring loaded spool retracts said cord for re-engagement of said plug and said lower housing.

3. The electrical automotive air freshener recited in claim 2, wherein said engaging means is a suction cup.

4. The electrical automotive air freshener recited in claim 2, wherein said engaging means comprises mating hook and loop fastener elements.

5. The electrical automotive air freshener recited in claim 2, further including a filter element disposed between said fragrance egress apertures and said scented oil, said filter element being porous enough to permit the vapor to pass through while restricting the passage of oil therethrough thus retaining said scented oil.

6. The electrical automotive air freshener recited in claim 1 in which an outer wall of said lower housing has an on/off temperature slide switch for adjusting intensity of emitted fragrance by adjusting heat delivered to the oil within the chamber.

* * * * *